(12) United States Patent
Lin

(10) Patent No.: US 8,981,193 B2
(45) Date of Patent: Mar. 17, 2015

(54) CULTIVAR, METHOD FOR DIFFERENTIATING PLANT CULTIVARS, AND METHOD FOR CAUSING EARLIER MATURING OF RICE INDIVIDUAL

(75) Inventor: Shaoyang Lin, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/005,211

(22) PCT Filed: Mar. 18, 2011

(86) PCT No.: PCT/JP2011/056548
§ 371 (c)(1),
(2), (4) Date: Sep. 13, 2013

(87) PCT Pub. No.: WO2012/127558
PCT Pub. Date: Sep. 27, 2012

(65) Prior Publication Data
US 2014/0109248 A1 Apr. 17, 2014

(51) Int. Cl.
*A01H 1/00* (2006.01)
*C12Q 1/68* (2006.01)
*A01H 5/00* (2006.01)
*C12N 15/82* (2006.01)
*A01H 5/10* (2006.01)

(52) U.S. Cl.
CPC ............. *C12N 15/8266* (2013.01); *A01H 5/10* (2013.01); *C12Q 1/6895* (2013.01); *A01H 5/00* (2013.01); *C12Q 2600/156* (2013.01)
USPC ........ 800/320.2; 800/260; 800/267; 800/266; 435/410; 435/6.11

(58) Field of Classification Search
USPC ............................................. 800/320.2, 267
See application file for complete search history.

(56) References Cited

U.S. PATENT DOCUMENTS

| | | | |
|---|---|---|---|
| 7,566,815 | B2 | 7/2009 | Takano et al. |
| 2006/0123507 | A1 | 6/2006 | Ashikari et al. |
| 2008/0320611 | A1 | 12/2008 | Takashi et al. |

FOREIGN PATENT DOCUMENTS

| | | |
|---|---|---|
| JP | 2008-283902 A | 11/2008 |
| JP | 4352102 B1 | 10/2009 |
| JP | 4368391 B2 | 11/2009 |
| JP | 2010-011826 A | 1/2010 |
| JP | 4409610 B2 | 2/2010 |
| JP | 2011-513769 | 4/2011 |
| JP | 4892647 B1 | 3/2012 |
| WO | WO 03/070934 A1 | 8/2003 |
| WO | WO 2004/044200 A1 | 5/2004 |

OTHER PUBLICATIONS

International Search Report, PCT/JP2011/056548 dated Apr. 19, 2011
Japanese Office Action, Application No. 2011-513784, dated Jun. 14, 2011.
Mayuko Ikeda, et al., "Tashu Ine, Habataki no Ho no Chakuryu Kozo Keisei ni Kakawaru Gni Oyobi QTL no Pyramiding", Breeding research, Sep. 24, 2010, (Sep. 24, 2010), vol. 12, seperate vol. 2, p. 253.
RGP:http://rgp.dna.affrc.go.jp/E/publicdata.html.
Taiichiro Okawa, "(9) Ko-Biomass Tashusei Suito Chokan Hinshu ga Sonaeru beki Tai-Tofukusei ni Kan'yo suru Kyoku-Kyokan Keishitsu no QTL Kaiseki", Kenkyu Seika Dai 471 Shu 'Genome Ikushu ni yoru Koritsuteki Hinshu Ikusei Gijutsu no Kaihatsu, QTL Idenshi Kaiseki no Suishin', Feb. 20, 2009 (Feb. 20, 2009) pp. 60 to 63.
Takahashi, et al., PNAS (2001), vol. 98, No. 14, p. 7922-7927.

*Primary Examiner* — Medina A Ibrahim
(74) *Attorney, Agent, or Firm* — Carrier Blackman & Associates, P.C.; Joseph P. Carrier; Fulchand P. Shende

(57) ABSTRACT

An object of the present invention is to provide a new rice cultivar that matures earlier than the original cultivar, and a method for causing a rice individual to mature earlier. The present invention relates to a rice cultivar Koshihikari kazusa no. 5 having the cultivar registration application number 25586, a progeny individual obtained by crossbreeding two individuals selected from the group consisting of an individual of the aforementioned cultivar and a progeny individual thereof, and a method for causing a rice individual to mature earlier that comprises replacing a region corresponding to a region containing base number 31,720,064 to base number 31,724,043 of the third chromosome of rice cultivar Nipponbare with a chromosome fragment composed of the corresponding region of rice cultivar Koshihikari kazusa no. 5 or rice cultivar Habataki in the third chromosome of the rice individual.

8 Claims, 7 Drawing Sheets

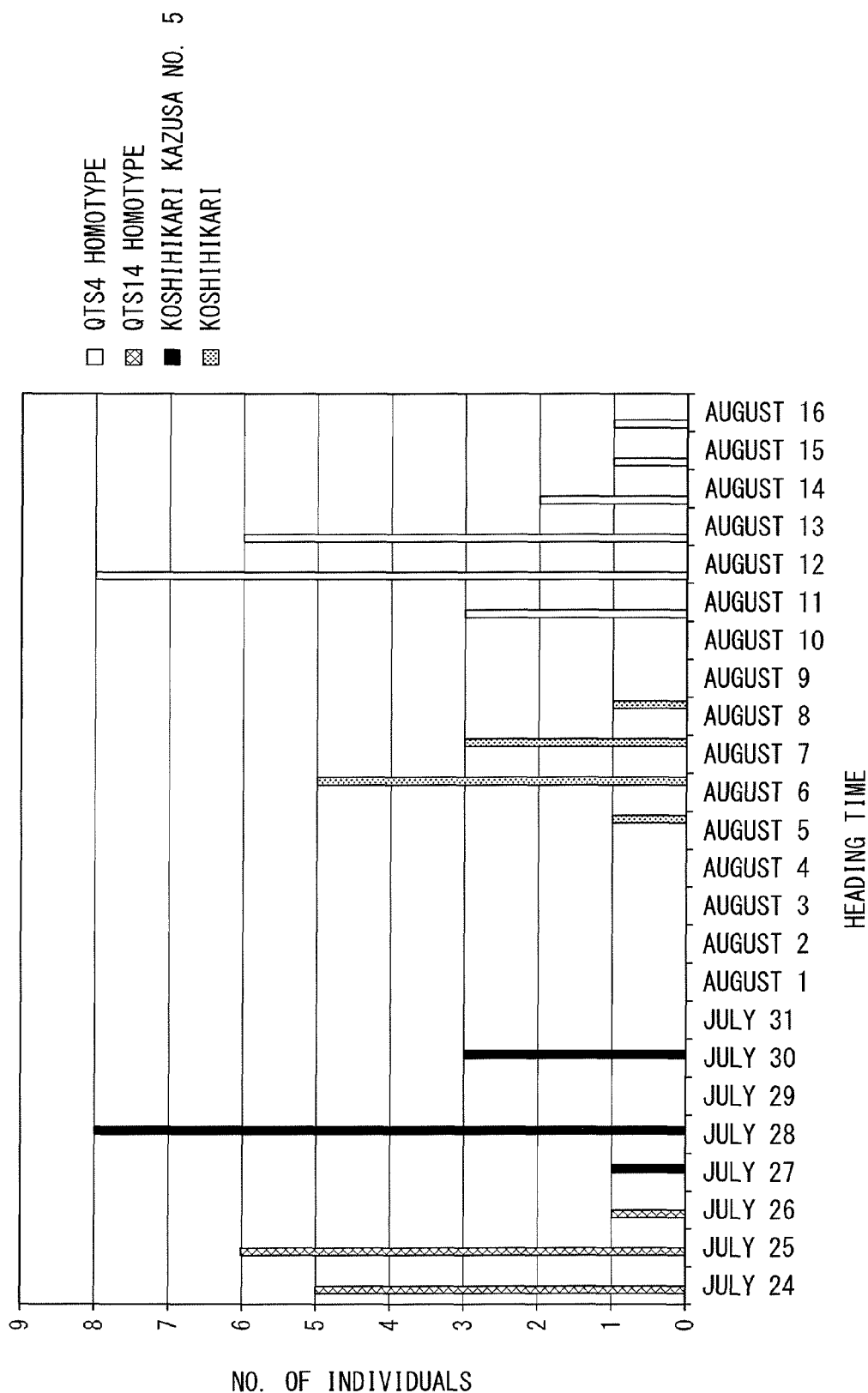

CULTIVAR, METHOD FOR DIFFERENTIATING PLANT CULTIVARS, AND METHOD FOR CAUSING EARLIER MATURING OF RICE INDIVIDUAL

CROSS-REFERENCE TO RELATED APPLICATIONS

This application is a National Stage entry of International Application No. PCT/JP2011/056548, filed Mar. 18, 2011. The disclosure of the prior application is hereby incorporated in their entirety by reference.

SEQUENCE LISTING

The instant application contains a Sequence Listing which has been submitted in ASCII format via EFS-Web and is hereby incorporated by reference in its entirety. Said ASCII copy, is named OSP48660.txt and is bytes 3.08 KB in size.

TECHNICAL FIELD

The present invention relates to a new cultivar produced by a non-genetic recombination method, a method for differentiating that new cultivar, and a method for early maturing of a rice individual.

BACKGROUND ART

A population that belongs to the same species, but differs from other populations in terms of a certain trait as a result of having a different genetic composition, is referred to as a cultivar. In other words, even within the same species of plant, cultivation difficulty, resistance to damage caused by diseases and insects, yield, quality and the like differ according to the particular cultivar. Consequently, in agricultural products and particularly in major crops such as rice, barley or wheat, cultivar improvement has been carried out extensively in order to obtain better cultivars, and in recent years, cultivar improvement has been aggressively implemented by not only nursery companies and other private firms, but also by government agencies at the national and prefectural levels.

Accompanying recent progress made in fields such as nucleic acid analysis technology, the genes of various plants such as thale cress, rice and wheat have been analyzed, and the resulting genetic information has been disclosed. Cultivar improvement consisting of introducing a gene from an introduced species using genetic recombination methods is being carried out extensively by using this disclosed genetic information. However, although cultivar improvement by genetic recombination has the advantage of being able to introduce a trait possessed by a distantly related species for which cross-breeding is normally not possible, there is the problem of not always being able to adequately verify the safety thereof.

Consequently, new cultivars are being extensively produced by non-genetic recombination methods in the case of edible plants including rice. For example, Patent Document 1 discloses a method for producing a new cultivar having a target trait, without altering preferable traits possessed by the original cultivar, by controlling a substitution region using a chromosome fragment derived from an introduced cultivar in the case of substituting with an exogenous useful chromosome fragment by a non-genetic recombination method.

In rice in particular, cultivars are desired to be bred that mature a little earlier or a little later than conventional cultivars while still maintaining the same quality and yield of the conventional cultivar. Although the rice cultivar, Koshihikari, is cultivated in the majority of rice paddies of Japan since it is preferred by consumers, in the case of cultivating only Koshihikari on a large scale, harvesting-related work becomes concentrated in a short time period and requires considerable labor. Although there is no guarantee that each individual can be harvested at the optimum time particularly in the case of large-volume harvesting of rice, since harvesting the plants too early or too late has an effect on the flavor and yield of the rice, this presents a considerable problem for rice farmers. One possible method for shifting the harvesting time is to shift the seeding time. However, since Koshihikari is highly sensitive to light, even if the seeding time is shifted by only 2 or 3 days, it reaches the harvesting time at the same time. On the other hand, the harvesting time can be dispersed by shifting the seeding time by 10 days or more. However, in the case of making a considerable shift in the seeding time, the growing period becomes shorter, thereby resulting in the problem of being unable to obtain an adequate yield. If it were possible to cultivate a cultivar that matures a little earlier or a little later along with conventional cultivars, since this would make it possible to shift the harvesting time, harvesting work could be expected to be carried out while shifting the harvesting time for each cultivar.

However, the development of a cultivar that matures a little earlier or a little later than conventional cultivars, namely a Koshihikari cultivar that has been slightly adjusted so as to slightly shift the heading time or harvesting time thereof, is technically extremely difficult. This is because it is difficult to detect slight differences in heading time and specify a particular gene related thereto. In order to genetically detect such a slight difference in heading time, it is not sufficient to merely require a precise field at which soil and fertilization of the rice paddy, water, air flow and other conditions of the field environment are extremely uniform, but is also necessary for the status of the seeds used for seeding to also be uniform, and this is in fact extremely difficult. In actuality, in rice paddies in Japan, even among genetically identical cultivars, there is normally a deviation of about 7 days even if seeded on the same day and planted on the same day. In other words, there may be as many as 7 days between the day on which heading is first observed and the last day on which it is observed. Although fields of considerably high precision are used in the case of agricultural test fields and the like, there is still typically a shift of 3 to 5 days.

PRIOR ART DOCUMENTS

Patent Documents

[Patent Document 1] Japanese Patent No. 4409610

DISCLOSURE OF THE INVENTION

Problems to be Solved by the Invention

An object of the present invention is to provide a new rice cultivar that matures earlier than the original cultivar, and a method for causing a rice individual to mature earlier.

Means for Solving the Problems

As a result of conducting extensive studies to solve the aforementioned problems, the inventor of the present invention found that harvesting time can be made to be earlier than Koshihikari by substituting a chromosome fragment of a specific region present on the third chromosome of the rice cultivar Habataki into the rice cultivar Koshihikari, thereby leading to completion of the present invention.

Namely, the present invention provides the following:

(1) a rice cultivar Koshihikari kazusa no. 5 (*Oryza sativa L.* cultivar Koshihikari kazusa no. 5) having the cultivar registration application number 25586;

(2) a progeny individual obtained by crossbreeding two individuals selected from the group consisting of an individual of the cultivar described in (1) above and a progeny individual of the individual of the cultivar described in (1) above;

(3) a method for differentiating rice cultivars: including, determining whether or not a certain rice cultivar is a specific cultivar, wherein an SNP (single nucleotide polymorphism) corresponding to the 31,521,442$^{nd}$ SNP in the third chromosome of rice cultivar Nipponbare (A in rice cultivar Koshihikari and C in rice cultivar Habataki) is designated as DNA marker M1, an SNP corresponding to the 31,689,690$^{th}$ SNP of the third chromosome of rice cultivar Nipponbare (C in rice cultivar Koshihikari and T in rice cultivar Habataki) is designated as DNA marker M2, an SNP corresponding to the 32,208,924$^{th}$ SNP of the third chromosome of rice cultivar Nipponbare (A in rice cultivar Koshihikari and G in rice cultivar Habataki) is designated as DNA marker M3, an SNP corresponding to the 32,363,157$^{th}$ SNP of the third chromosome of rice cultivar Nipponbare (A in rice cultivar Koshihikari and T in rice cultivar Habataki) is designated as DNA marker M4, an SNP corresponding to the 32,384,799$^{th}$ SNP of the third chromosome of rice cultivar Nipponbare (T in rice cultivar Koshihikari and G in rice cultivar Habataki) is designated as DNA marker M5, one or more DNA markers selected from the group consisting of the DNA markers M1 to M5 are typed by genome analysis of the rice individual, and in the case the resulting typing result coincides with the result for rice cultivar Koshihikari kazusa no. 5 (*Oryza sativa L.* cultivar Koshihikari kazusa no. 5), the rice individual is identified as rice cultivar Koshihikari kazusa no. 5;

(4) a method for causing a rice individual to mature earlier, including: replacing a region corresponding to a region containing base number 31,720,064 to base number 31,724,043 of the third chromosome of rice cultivar Nipponbare with a chromosome fragment composed of the corresponding region of rice cultivar Koshihikari kazusa no. 5 or rice cultivar Habataki in the third chromosome of the rice individual;

(5) a method for causing a rice individual to mature earlier, including: replacing a region corresponding to a region containing base number 31,720,064 to base number 32,314,677 of the third chromosome of rice cultivar Nipponbare with a chromosome fragment composed of the corresponding region of rice cultivar Koshihikari kazusa no. 5 or rice cultivar Habataki in the third chromosome of the rice individual;

(6) the method for causing a rice individual to mature earlier described in (5) above, wherein the chromosome fragment is replaced so that the upstream end of the chromosome fragment is present in a region corresponding to a region containing base number 31,689,691 to base number 31,720,064 of the third chromosome of rice cultivar Nipponbare, and the downstream end of the chromosome fragment is present in a region corresponding to a region containing base number 32,314,677 to base number 32,363,156 of the third chromosome of rice cultivar Nipponbare;

(7) a method for causing a rice individual to mature earlier, including: replacing a region corresponding to a region containing base number 31,689,690 to base number 32,363,157 of the third chromosome of rice cultivar Nipponbare with a chromosome fragment composed of the corresponding region of rice cultivar Koshihikari kazusa no. 5 or rice cultivar Habataki in the third chromosome of the rice individual;

(8) the method for causing a rice individual to mature earlier described in (7) above, wherein the chromosome fragment is replaced so that the upstream end of the chromosome fragment is present in a region corresponding to a region containing base number 31,521,443 to base number 31,689,690 of the third chromosome of rice cultivar Nipponbare, and the downstream end of the chromosome fragment is present in a region corresponding to a region containing base number 32,363,157 to base number 32,384,798 of the third chromosome of rice cultivar Nipponbare;

(9) a rice cultivar produced by the method for causing a rice individual to mature earlier described in any of (4) to (8) above;

(10) a progeny individual obtained by crossbreeding two individuals selected from the group consisting of an individual of the cultivar described in (9) above and a progeny individual of the individual of the cultivar described in (9) above;

(11) a method for causing a rice individual to mature later, including: replacing a region corresponding to a region containing base number 32,309,502 to base number 32,314,677 of the third chromosome of rice cultivar Nipponbare with a chromosome fragment composed of the corresponding region of rice cultivar Koshihikari kazusa no. 5 or rice cultivar Habataki in the third chromosome of the rice individual;

(12) a rice cultivar produced according to the method for causing a rice individual to mature later described in (11) above; and,

(13) a progeny individual obtained by crossbreeding two individuals selected from the group consisting of an individual of the cultivar described in (12) above and a progeny individual of the individual of the cultivar described in (12) above.

Effects of the Invention

Although the new cultivar of the present invention in the form of rice cultivar Koshihikari kazusa no. 5 matures earlier than Koshihikari, characteristics other than harvesting time, such as quality or yield, are nearly the same as those of Koshihikari.

In addition, rice individuals can be made to mature earlier than the original cultivar by using the method of the present invention for causing a rice individual to mature earlier.

BRIEF DESCRIPTION OF THE DRAWINGS

FIG. 7 is a drawing showing the results of investigating the heading times of Koshihikari kazusa no. 5, Koshihikari, a QTS4 homotype and a QTS14 homotype.

BEST MODE FOR CARRYING OUT THE INVENTION

Figure 1:
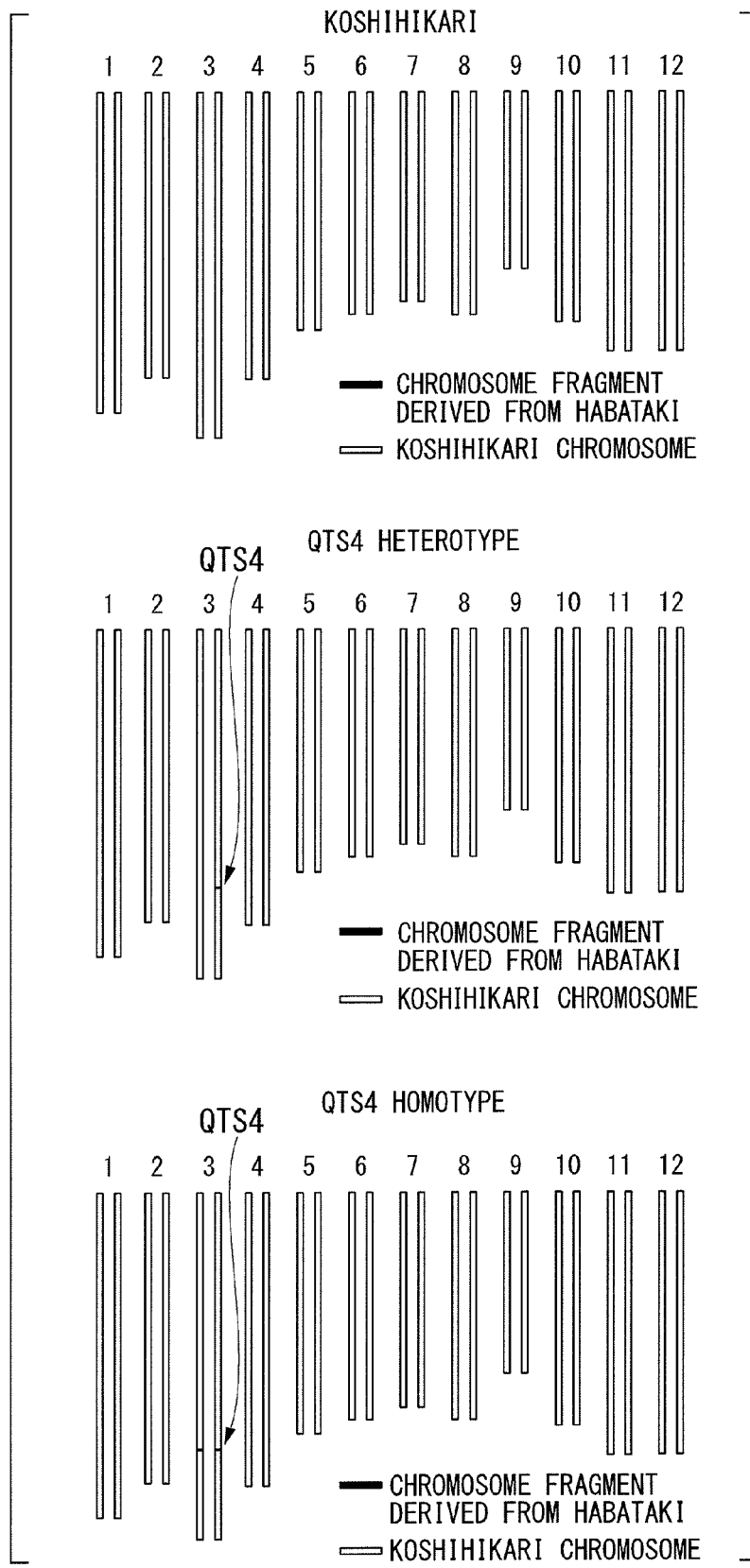
FIG. 1 is a drawing schematically representing the genomes of Koshihikari, a QTS4 heterotype and a QTS4 homotype.

A modified chromosome fragment strain in the present invention refers to a stain in which only a portion of a chromosome of the original cultivar has been replaced with a chromosome fragment derived from an introduced cultivar. Here, there are no particular limitations on the introduced cultivar provided it is a cultivar other than the original cultivar, and maybe a cultivar of a plant of the same species as the original cultivar, may be a cultivar of a plant of a different species than the original cultivar, or may be a cultivar other than a plant cultivar such as that of an animal. Furthermore, in the present invention, a cultivar refers to a population that belongs to the same plant species and can be clearly differentiated from other cultivars of the same species in terms of a certain trait as a result of having a different genetic composition.

In the present invention, there are no particular limitations on DNA markers provided they allow the detection of differences in DNA sequences in chromosomes that enables differentiation between a chromosome derived from an original cultivar and a chromosome derived from an introduced cultivar, and DNA markers normally used in the field of genetic analysis can be used. These DNA markers may be markers capable of detecting genetic polymorphisms such as differences in the number of repeats of single nucleotide polymorphisms (SNP) or simple sequence repeats (SSR), or may be restrictive fragment length polymorphisms (RFLP) markers. Furthermore, differentiation between an allele derived from an original cultivar and an allele derived from an introduced cultivar by these DNA markers can be carried out in accordance with ordinary methods. For example, each polymorphism can be differentiated by carrying out PCR using DNA extracted from each individual as template and using primers and the like capable of specifically hybridizing with a specific SNP or SSR, and then detecting the presence or absence of the PCR product using electrophoresis and the like. In addition, each polymorphism can be differentiated by treating DNA extracted from each individual with restrictase and then detecting the pattern of a DNA fragment using electrophoresis and the like. Furthermore, primers and the like capable of specifically hybridizing with a specific SNP or SSR can be designed in accordance with ordinary methods using commonly used primer design tools and the like corresponding to the base sequence of the SNP or SSR. In addition, designed primers and the like can be synthesized using any method well known in the relevant technical field.

Known DNA markers can be suitably used for these DNA markers. In addition, these DNA markers may also be newly produced DNA markers. Examples of known DNA markers that can be used in rice include the SNP markers disclosed in international Publication No. WO 2003/070934 and DNA markers publicly disclosed by the Rice Genome Research Program on its website.

Furthermore, enetic information on each cultivar can be acquired from the international base sequence databases of the National Center for Biotechnology Information (NCBI) or the DNA Data Bank of Japan (DDBJ). Genetic information on each rice cuitivar in particular can be acquired from the Knowledge-based *Oryza* Molecular biological Encyclopedia available on the internet (i.e., the cdna0 website).

In the present invention and description of the present application, a "region from base number X to base number Y of a chromosome of the rice cultivar Nipponbare" is a region determined based on the base sequence of genomic DNA of the rice cultivar Nipponbare publicly disclosed by RGB (Version 4: IRGSP-build4-06/04/21).

In addition, in the present invention and description of the present application, a "region corresponding to a region from base number X to base number Y of a chromosome of rice cultivar Nipponbare" is a region in a chromosome of a rice individual that is highly homologous with the corresponding sequence in a chromosome of rice cultivar Nipponbare, and can be determined by aligning the base sequences of known genomic DNA of rice cultivar Nipponbare and genomic DNA of the rice individual so as to demonstrate the highest homology. In addition, an "SNP corresponding to an SNP of rice cultivar Nipponbare" in a rice individual other than rice cultivar Nipponbare refers to a base at a location corresponding to the SNP within a region containing the SNP in the case the base sequences of known genomic DNA of rice cultivar Nipponbare and genomic DNA of the rice individual have been aligned so as to demonstrate the highest homology.

In order to breed a new cultivar that matures a little earlier or a little later than a conventional cultivar, the inventor of the present invention first conducted a quantitative trait locus (QTL) analysis of heading time in an isolated population by crossbreeding rice cultivar Habataki and rice cultivar Koshihikari. As a result, a QTL that results in late maturation by delaying heading time was determined to be present in the QTS4 region of the long arm of the third chromosome. Rice that matures later than the original Koshihikari cultivar was predicted to be obtained by replacing a gene contained in the corresponding region of Koshihikari with a gene derived from Habataki.

Figure 2:
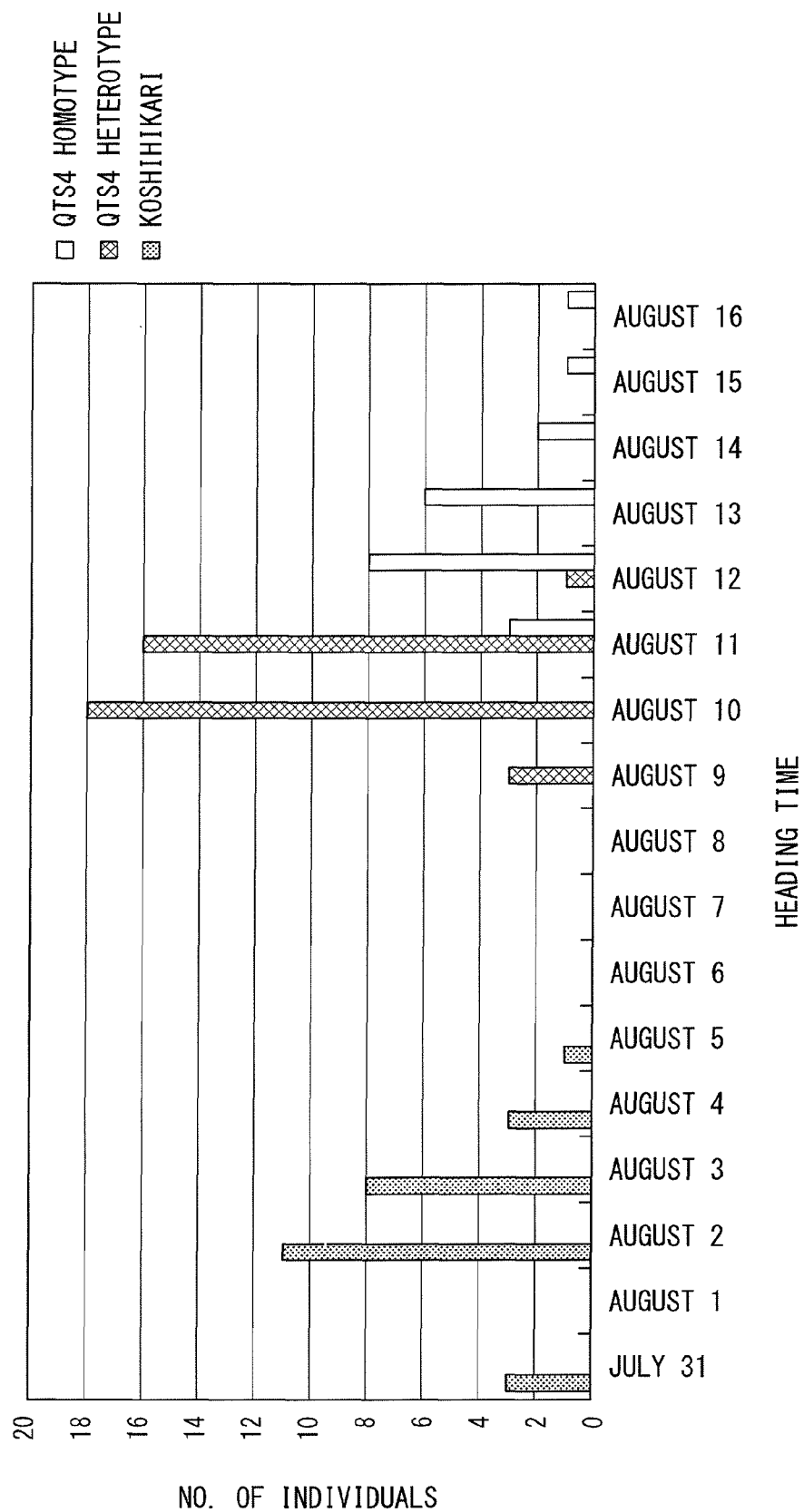
FIG. 2 is a drawing showing the results of investigating the heading times of Koshihikari, a QTS4 heterotype and a QTS4 homotype.

Therefore, a modified chromosome fragment strain was produced in which a QTS4 region of Koshihikari (region corresponding to a region from base number 32,309,502 to base number 32,314,677 of the third chromosome of rice cultivar Nipponbare) was replaced with a chromosome fragment derived from Habataki by back crossbreeding with Koshihikari. At this time, individuals of both a QTS4 heterotype, in which only the QTS4 region of one homologous chromosome was replaced with the Habataki-derived chromosome fragment, and a QTS4 homotype, in which the QTS4 regions of both homologous chromosomes were replaced with the Habataki-derived chromosome fragment, were obtained. FIG. 1 is a drawing schematically representing the genomes of Koshihikari, the QTS4 heterotype and the QTS4 homotype. Moreover, when the heading time of each rice cultivar was measured in a field located in Chiba prefecture (seeding date: May 6, 2010, relocation date: Jun. 1, 2010), in contrast to the heading time of Koshihikari being from July 31 to August 5, that of the QTS4 heterotype was from August 9 to August 12, while that of the QTS4 homotype was from August 11 to August 16 as shown in FIG. 2. In other words, the QTS4 heterotype and the QTS4 homotype clearly matured later than the original Koshihikari cultivar, and that tendency was determined to be stronger for the QTS4 homotype than the QTS4 heterotype.

In addition, in a QTL analysis relating to heading time, a QTL that results in early maturation by advancing heading time was determined to be present in a QTS14 region of the long arm of the third chromosome of rice cultivar Habataki (region corresponding to a region from base number 31,720, 064 to base number 31,724,043 of the third chromosome of rice cultivar Nipponbare). Rice that matures earlier than the original Koshihikari cultivar was predicted to be obtained by replacing a gene contained in the corresponding region of Koshihikari with a gene derived from Habataki.

Figure 3:
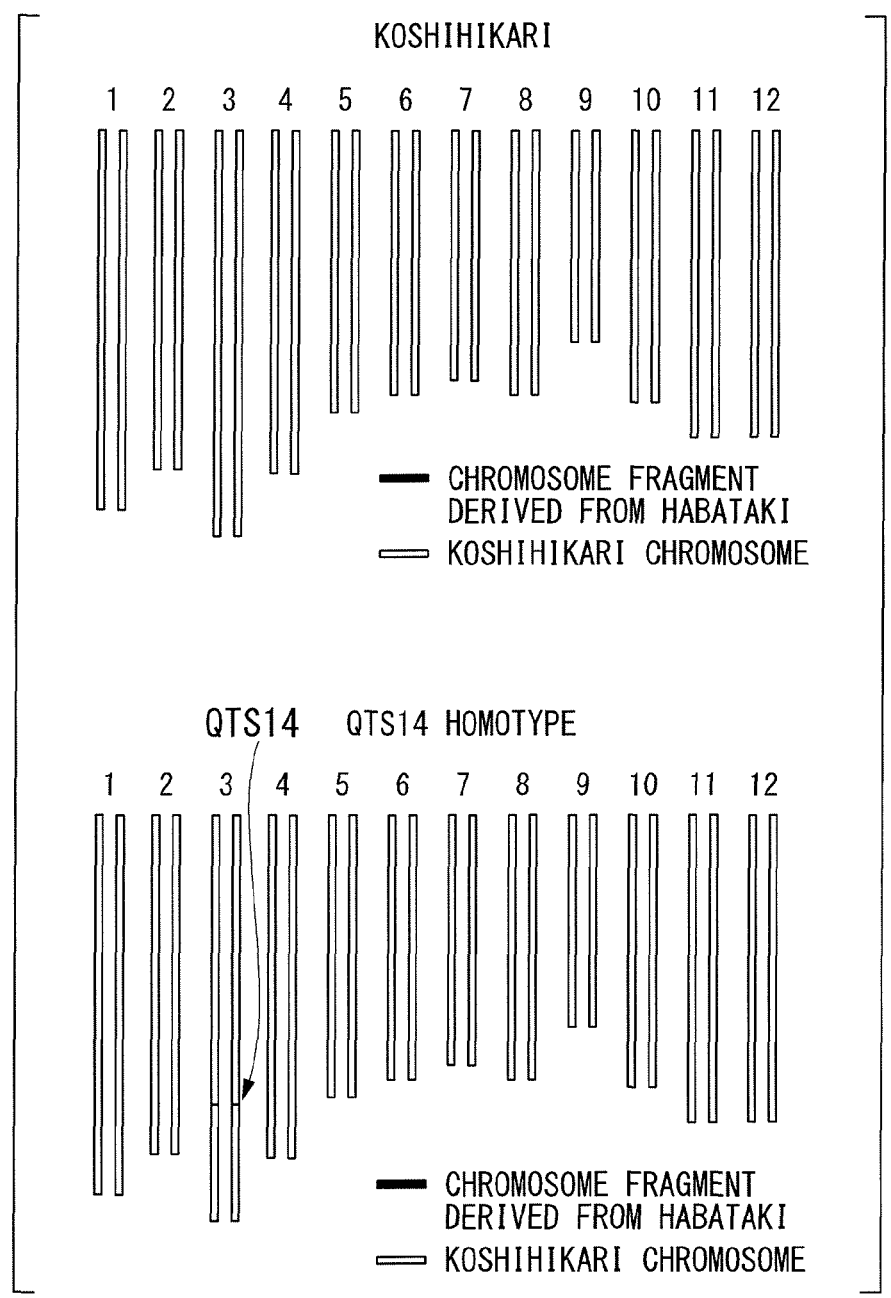
FIG. 3 is a drawing schematically representing the genomes of Koshihikari and a QTS14 homotype.
Figure 4:
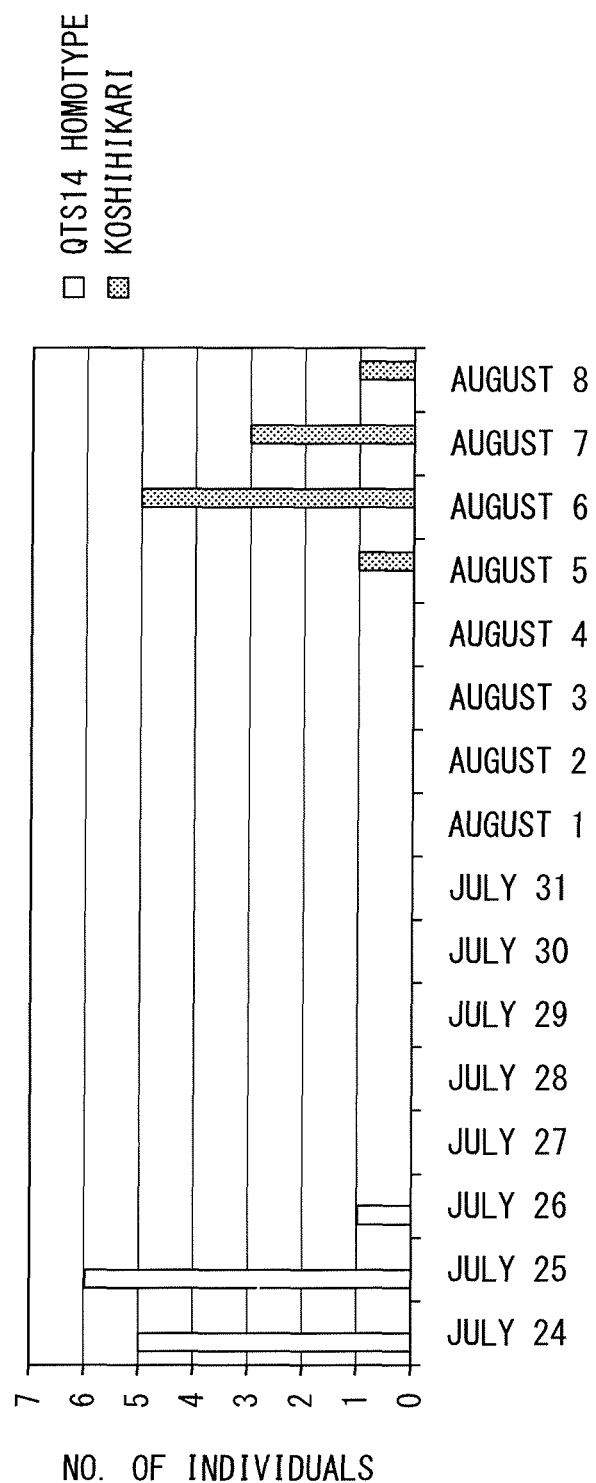
FIG. 4 is a drawing showing the results of investigating the heading times of Koshihikari and a QTS14 homotype.

Therefore, a modified chromosome fragment strain was produced in which the QTS14 region of Koshihikari was replaced with a gene fragment derived from Habataki by back crossbreeding with Koshihikari. FIG. 3 is a drawing schematically representing the genomes of Koshihikari and the QTS14 homotype. Moreover, when the heading time of each rice cultivar was measured in a field located in Chiba prefecture (seeding date: May 6, 2010, relocation date: Jun. 1, 2010), in contrast to the heading time of Koshihikari being from August 5 to August 8, that of the QST14 homotype was from July 24 to July 26 as shown in FIG. 4. In other words, the QTS14 homotype was clearly determined to mature earlier than the original Koshihikari cultivar.

On the basis of these results, the inventor of the present invention thought that it may be possible to develop a new cultivar that produces a slight difference in heading time from that of Koshihikari by replacing and introducing both a chromosome fragment that causes expression of the trait of late maturity contained in the Habataki-derived QTS4 region (to be referred to as the chromosome fragment causing late maturity) and a chromosome fragment that causes expression of the trait of early maturity contained in the Habataki-derived QTS14 region (to be referred to as the chromosome fragment causing early maturity) for the corresponding chromosome fragments of Koshihikari.

The QTS4 region and the QTS14 region are mutually adjacent. Consequently, the inventor of the present invention attempted to produce rice that matures a little earlier or a little later than Koshihikari by replacing and introducing a Habataki-derived chromosome fragment of a region that contains both regions and the region there between into Koshihikari.

In the case of plant cultivar improvement by a non-genetic recombination method, if the introduced chromosome fragment derived from an introduced cultivar is excessively large, there is the risk of introducing a large number of other genes of indeterminate function other than the gene for the target trait, as well as the risk of impairing preferable traits possessed by the original cultivar. Therefore, the inventor of the present invention produced a new cultivar according to the method described in Patent Document 1 in order to produce a new cultivar having a target trait, without altering preferable traits possessed by the original cultivar, by controlling a substitution region using a chromosome fragment derived from an introduced cultivar.

Figure 5:
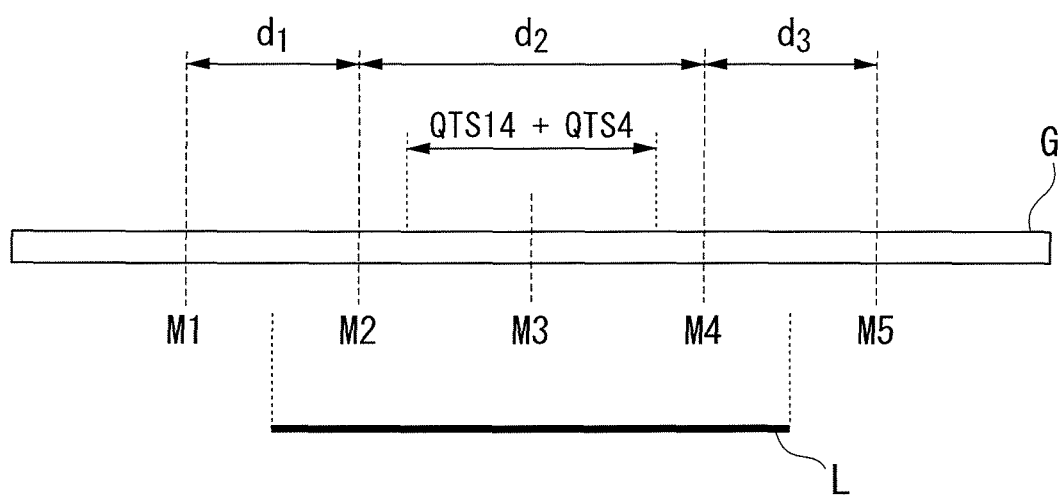
FIG. 5 is a drawing schematically indicating the locations of a QTS4 region, QTS14 region and DNA markers on the third chromosome of Koshihikari.

More specifically, five types of DNA markers having the positional relationships shown in FIG. 5 were first determined based on known rice genetic information. Namely, a DNA marker M2 was set for the upstream end of a region containing the QTS4 region and QTS14 region (to be referred to as the "(QTS4+QTS14) region") or upstream therefrom, a DNA marker M1 was set upstream from DNA marker M2, a DNA marker M4 was set for the downstream end of the (QTS4+QTS14) region or downstream therefrom, a DNA marker M5 was set downstream from the DNA marker M4, and a DNA marker M3 was set within the (QTS4+QTS14) region. Next, back crossbreeding was carried out on a modified chromosome fragment strain in which only a portion of the Koshihikari chromosome containing the (QTS4+QTS14) region was replaced with a chromosome fragment derived from Habataki, and preferable individuals based on the aforementioned five types of DNA markers M1 to M5 were selected from the resulting hybrid population. Subsequently, by suitably similarly repeating selection of preferable individuals based on DNA markers M1 to M5 by carrying out self-crossbreeding or back crossbreeding on the individuals, a progeny individual was obtained such that the upstream end of the region replaced by the Habataki-derived chromosome fragment ("L" in FIG. 5) is present between DNA markers M1 and M2, and the downstream end of that region is present between DNA markers M4 and M5. As shown in FIG. 5, in this progeny individual, DNA markers M1 and M5 are of the same type as the original Koshihikari cultivar, while DNA markers M2, M3 and M4 are of the same type as Habataki.

Here, in the method for producing a new cultivar described in Patent Document 2, if a distance d1 between DNA markers M1 and M2 is long, the range over which the upstream end of chromosome fragment L derived from an introduced cultivar (chromosome fragment derived from Habataki in the present application) can be present becomes large, thereby making it difficult to determine the length of the introduced Habataki-derived chromosome fragment L. On the other hand, if the distance d1 is short, the range over which the upstream end of the Habataki-derived chromosome fragment L can be present becomes small, thereby making it easy to determine the length of the introduced Habataki-derived chromosome fragment L. Similarly, if a distance d3 between DNA markers M4 and M5 is long, the range over which the downstream end of the Habataki-derived chromosome fragment L can be present becomes large, thereby making it difficult to determine the length of the introduced Habataki-derived chromosome fragment L, while if the distance d3 is short, the range over which the downstream end of the Habataki-derived chromosome fragment L can be present becomes small, thereby making it easy to determine the length of the introduced Habataki-derived chromosome fragment L.

As the length of the Habataki-derived chromosome fragment L increases, there is an increasing possibility of genes present in regions other than the QTS4 region and QTS14 region being introduced into the original Koshihikari cultivar together with target genes present in the QTS4 region and QTS14 region. Since the introduction of genes other than the target genes results in replacement of genes other than the target gene present in the original cultivar, there is the risk of superior traits possessed by the original cultivar being inadvertently impaired. Consequently, the length of the Habataki-derived chromosome fragment L is preferably not any longer than what is necessary in comparison with the shortest region containing the QTS4 region and QTS14 region (region from the upstream end of QTS14 to the downstream end of QTS4, and to be referred to as the "(QTS4+QTS14) region").

The inventor of the present invention established a plurality of sets of DNA markers M1 to M5 and produced a plurality of individuals into which were introduced chromosome fragments of different lengths containing the (QTS4+QTS14) region, followed by investigating the heading time of each individual. As a result, all of the individuals were early maturing individuals in which heading time was a little earlier than that of Koshihikari. Moreover, when traits other than heading time of each individual (such as flavor or yield) were compared with those of Koshihikari, individuals produced using each of the sets of DNA markers M1 to M5 (rice cultivar Koshihikari kazusa no. 5 (*Oryza sativa* L. cultivar Koshihikari kazusa no. 5)) shown in Table 1, namely by using an SNP (single nucleotide polymorphism) corresponding to the 31,521,442nd SNP of the third chromosome of rice cultivar Nipponbare (A in rice cultivar Koshihikari and C in rice cultivar Habataki) for DNA marker M1 (DNA Marker M1-Ac), using an SNP corresponding to the 31,689,690$^{th}$ SNP of the third chromosome of rice cultivar Nipponbare (C in rice cultivar Koshihikari and T in rice cultivar Habataki) for DNA marker M2 (DNA marker M2-Ct), using an SNP corresponding to the 32,208,924$^{th}$ SNP of the third chromosome of rice cultivar Nipponbare (A in rice cultivar Koshihikari and Gin rice cultivar Habataki) for DNA marker M3 (DNA marker M3-Ag), using an SNP corresponding to the 32,363,157$^{th}$ SNP of the third chromosome of rice cultivar Nipponbare (A in rice cultivar Koshihikari and T in rice cultivar Habataki) for DNA marker M4 (DNA marker M4-Gc), and using an SNP corresponding to the 32,384,799$^{th}$ SNP of the third chromosome of rice cultivar Nipponbare (T in rice cultivar Koshihikari and Gin rice cultivar Habataki) for DNA marker M5 (DNA marker M5-Tg), were determined to have traits other than heading time that were the same as those of Koshihikari as indicated in Example 1 to be subsequently described (see Tables 2 to 5). Furthermore, rice cultivar Koshihikari kazusa no. 5 is an individual produced using a DNA marker set in which the length of the introduced Habataki-derived chromosome fragment is the shortest among DNA marker sets used to develop new cultivars.

to DNA marker M4-At (namely, a region corresponding to the region containing base number 31,689,690 to base number 32,363,157 of the third chromosome of rice cultivar Nipponbare) with a chromosome fragment composed of the corresponding region of the rice cultivar Habataki in the third chromosome of the rice individual. Furthermore, since the corresponding region of rice cultivar Koshihikari kazusa no. 5 is composed by a chromosome fragment composed of the corresponding region of rice cultivar Habataki, it may also be replaced with a chromosome fragment composed of the corresponding region of rice cultivar Koshihikari kazusa no. 5. In addition, a rice individual that has been made to mature earlier by introducing a chromosome fragment composed of the corresponding region of rice cultivar Habataki is a cultivar in which the corresponding region has a base sequence that is identical or similar to rice cultivar Koshihikari, and although it is not limited to rice cultivar Koshihikari, in consideration

TABLE 1

| Marker | Location in 3$^{rd}$ chromosome | Koshihikari type | Habataki type | Sequence |
|---|---|---|---|---|
| M1-Ac | 31,521,442 | A | C | Upper primer: CATTCAGTTCTCTCAACTGC (SEQ ID NO: 1)<br>Lower primer: GAGATTTTCGAAGGTTCTTCGC (SEQ ID NO: 2)<br>SNP primer: TTCCTAACCCAGCTGTGAT (SEQ ID NO: 3) |
| M2-Ct | 31,689,690 | C | T | Upper primer: AAAACAGCCACACCTGATCG (SEQ ID NO: 4)<br>Lower primer: AACATCCTCTGCTTCCTCAG (SEQ ID NO: 5)<br>SNP primer: TATCGCTAGCCTCCATTTCT (SEQ ID NO: 6) |
| M3-Ag | 32,208,924 | A | G | Upper primer: GAATGGAATGAGCCATACTCC (SEQ ID NO: 7)<br>Lower primer: CTGCATCTACACGCTATACC (SEQ ID NO: 8)<br>SNP primer: GTGATGGAAAAGTTGGAAGTTTGAA (SEQ ID NO: 9) |
| M4-Gc | 32,363,157 | A | T | Upper primer: ACGTGGGGTACAGCACTTTGA (SEQ ID NO: 10)<br>Lower primer: GTCAGGAAAGTTGGAAGAGG (SEQ ID NO: 11)<br>SNP primer: GATCTCTGACAATATCAAGAAGCT (SEQ ID NO: 12) |
| M5-Tg | 32,384,799 | T | G | Upper primer: TCTGAGTATCTGACTCCACG (SEQ ID NO: 13)<br>Lower primer: CTCTCCTGTCTTAGAAGAAGAC (SEQ ID NO: 14)<br>SNP primer: CAAAGTTGGCAACTCGGCATA (SEQ ID NO: 15) |

Koshihikari kazusa no. 5 is a new cultivar produced according to the method described in Patent Document 1, and despite maturing somewhat earlier than Koshihikari, is an extremely superior cultivar in that it maintains the flavor and other superior traits possessed by Koshihikari. Therefore, the applicant applied for cultivar registration for Koshihikari kazusa no. 5 as defined in the Seed and Seedlings Law of Japan (Law No. 83, May 29, 1998) (cultivar registration application filing date: Jan. 28, 2011, cultivar registration application number: 25586).

On the basis of these results, the rice individuals were clearly able to mature earlier than the original cultivar as a result of replacing at least a region from DNA marker M2-Ct of consumer preferences and the like, it is preferably rice cultivar Koshihikari or a new cultivar produced by using it as a parent cultivar.

In addition, a rice individual can be made to mature earlier than the original cultivar without having significant effects on traits other than heading time by introducing a chromosome fragment into the third chromosome of the rice individual so that the upstream end of the chromosome fragment derived from an introduced rice cultivar Habataki (or derived from rice cultivar Koshihikari kazusa no. 5) is present in a region that is downstream from DNA marker M1-Ac and extends to DNA marker M2-Ct (namely, a region corresponding to a region containing base number 31,521,443 to base number 31,689,690 of the third chromosome of rice cultivar Nipponbare), and the downstream end thereof is present in a region extending from DNA marker M4-At to upstream from DNA marker M5-Tg (namely, a region corresponding to a region containing base number 32,363,157 to base number 32,384,798 of the third chromosome of rice cultivar Nipponbare).

When genes contained in the QTS4 region were investigated, heading time QTL gene Hd6 discovered in rice cultivar Nipponbare and rice cultivar Caracas was found to be contained in the vicinity of 32.3 Mbp of the third chromosome of that region. Hd6 has been reported to contain a region that encodes the casein kinase II subunit alpha gene (Takahashi, et al., PNAS (2001), Vol. 98, No. 14, p. 7922-7927). In addition, the region encoding that gene in rice cultivar Habataki has a different sequence than the allele of rice cultivar Koshihikari. Accordingly, the causative gene responsible for inducing late maturation in the QTS4 region is presumed to be the casein kinase II subunit alpha gene. In actuality, when the base sequence in the vicinity of 32.3 Mbp of the third chromosome of rice cultivar Koshihikari kazusa no. 5 was analyzed, the entire region that encodes that gene in rice cultivar Habataki was confirmed to be contained in a chromosome fragment derived from rice cultivar Habataki that had been introduced into the rice individual chromosome by substitution.

Furthermore, the casein kinase II subunit alpha gene has been mapped in the region from base number 32,309,502 to base number 32,314,677 of the third chromosome in the allelic fragment of rice cultivar Nipponbare, and in the region from base number 32,350,406 to base number 32,362,686 in the allelic fragment of the publicly disclosed rice cultivar Caracas. Thus, a rice individual can be made to mature later by replacing the region corresponding to the region containing base number 32,309,502 to base number 32,314,677 of the third chromosome of rice cultivar Nipponbare with a chromosome fragment composed of the corresponding region of rice cultivar Koshihikari kazusa no. 5 or rice cultivar Habataki in the third chromosome of the rice individual.

Similarly, when genes contained in the QTS14 region were investigated, a region encoding phytochrome C gene was contained in the vicinity of 31.7 Mbp of the third chromosome of that region. This gene has been reported to be mainly involved in plant flowering time (U.S. Pat. No. 7,566,815). Accordingly, the causative gene responsible for early maturation in the QTS14 region is presumed to be phytochrome C gene.

Furthermore, phytochrome C gene has been mapped in a region from base number 31,720,064 to base number 31,724,043 of the third chromosome in rice cultivar Nipponbare. Thus, a rice individual can be made to mature earlier by replacing the region corresponding to the region containing base number 31,720,064 to base number 31,724,043 of the third chromosome of rice cultivar Nipponbare with a chromosome fragment composed of the corresponding region of rice cultivar Koshihikari kazusa no. 5 or rice cultivar Habataki in the third chromosome of the rice individual.

If a region containing the causative gene of late maturation in the QTS4 region and the causative gene of early maturation in the QTS14 region is replaced with a Habataki-derived chromosome fragment, early maturation is thought to be induced in the same manner as rice cultivar Koshihikari kazusa no. 5 even in the case of a rice individual in which a region shorter than the region from DNA marker M2-Ct to DNA marker M4-At has been replaced by the Habataki-derived chromosome fragment. For example, a rice individual is thought to be able to be made to mature earlier than the original cultivar by replacing a region corresponding to the region containing base number 31,720,064 to base number 32,314,677 of the third chromosome of rice cultivar Nipponbare with a chromosome fragment composed of the corresponding region of rice cultivar Koshihikari kazusa no. 5 or rice cultivar Habataki in the chromosome of the rice individual. In addition, at that time, the rice individual is thought to be able to be made to mature earlier than the original cultivar without having significant effects on traits other than heading time by introducing the chromosome fragment into the third chromosome of the rice individual so that the upstream end of the chromosome fragment is present in a region corresponding to the region containing base number 31,689,691 to base number 31,720,064 of the third chromosome of rice cultivar Nipponbare, and the downstream end of the chromosome fragment is present in a region corresponding to the region containing base number 32,314,677 to base number 32,363,156 of the third chromosome of rice cultivar Nipponbare.

Rice cultivar Koshihikari kazusa no. 5 is a new cultivar in which heading time has been slightly advanced without having significant effects of other Koshihikari traits such as yield. Consequently, even if Koshihikari and Koshihikari kazusa no. 5 are seeded at roughly the same time, since Koshihikari kazusa no. 5 reaches heading time several days earlier than that of Koshihikari, Koshihikari can be harvested after first harvesting Koshihikari kazusa no. 5. As a result of shifting harvesting times in this manner, in addition to being able to disperse harvesting work even in the case of large-scale cultivation, since harvesting can be carried out at the proper time, rice having favorable flavor can be harvested.

Rice cultivar Koshihikari kazusa no. 5 can be cultivated in accordance with techniques similar to those used for the original Koshihikari cultivar, and rice can be harvested by self-crossbreeding or artificial crossbreeding. In addition, rice cultivar Koshihikari kazusa no. 5 and progeny individuals thereof can be used as parent individuals for developing new cultivars in the same manner as the original Koshihikari cultivar. For example, a new cultivar can be attempted to be developed by crossbreeding a rice cultivar Koshihikari kazusa no. 5 individual with an individual of a different cultivar, and then back crossbreeding the resulting progeny individual with an individual of rice cultivar Koshihikari kazusa no. 5.

In addition, the five types of DNA markers described in Table 1 (DNA marker M1-Ac, DNA marker M2-Ct, DNA marker M3-Ag, DNA marker M4-At and DNA marker M5-Tg) compose genomic information unique to rice cultivar Koshihikari kazusa no. 5. Thus, rice cultivar Koshihikari kazusa no. 5 can be differentiated by suitably using these five types of DNA markers.

More specifically, the method for differentiating rice cultivars of the present invention is a method for determining whether or not a certain rice individual is a specific cultivar, wherein one or more DNA markers selected from the group consisting of DNA marker M1-Ac, DNA marker M2-Ct, DNA marker M3-Ag, DNA marker M4-At and DNA marker M5-Tg are typed by genome analysis of the rice individual, and in the case the resulting typing result coincides with the result for rice cultivar Koshihikari kazusa no. 5, namely in the case DNA marker M1-Ac is adenine (A), DNA marker M2-Ct is thymine (T), DNA marker M3-Ag is guanine (G), DNA marker M4-At is T and DNA marker M5-Tg is T, the rice individual can be determined to be rice cultivar Koshihikari kazusa no. 5.

Here, in order to differentiate rice cultivars, all DNA markers M1 to M5 may be used or only several of the five DNA markers may be used. For example, only DNA markers M1 and M2 may be used that serve as recombination points on the upstream side, only DNA markers M4 and M5 may be used that serve as recombination points on the downstream side, or only DNA markers M2 and M4 may be used. Suitably combining a plurality of DNA markers makes it possible to more precisely differentiate rice cultivars.

EXAMPLES

Although the following provides a more detailed explanation of the present invention by indicating examples thereof, the present invention is not limited to the following examples.

Example 1

A new cultivar in which harvesting time was made to be a little earlier than the original Koshihikari cultivar was produced by using as a parent individual a modified chromosome fragment strain in which only a portion of a chromosome of Koshihikari containing a (QTS4+QTS14) region was replaced with a chromosome fragment derived from Habataki.

First, the modified chromosome fragment strain and Koshihikari were crossbred, and 10 progeny individuals (seeds) were harvested in which DNA marker M3-Ag was a hetero chromosome region of the Koshihikari-derived allele and Habataki-derived allele. The resulting seeds were cultivated followed by allowing to self-propagate (self-crossbreed) and harvesting the progeny individuals in the form of seeds.

The harvested seeds were further cultivated. After growing to a degree that allowed them to be relocated to a field, DNA was recovered from the leaves of each individual, and cultivated individuals were selected in which DNA marker M1-Ac was a homo chromosome region for the Koshihikari-derived allele, and DNA markers M2-Ct and M3 (DNA marker M3-Ag) were hetero chromosome regions of the Koshihikari-derived allele and Habataki-derived allele.

Figure 6:
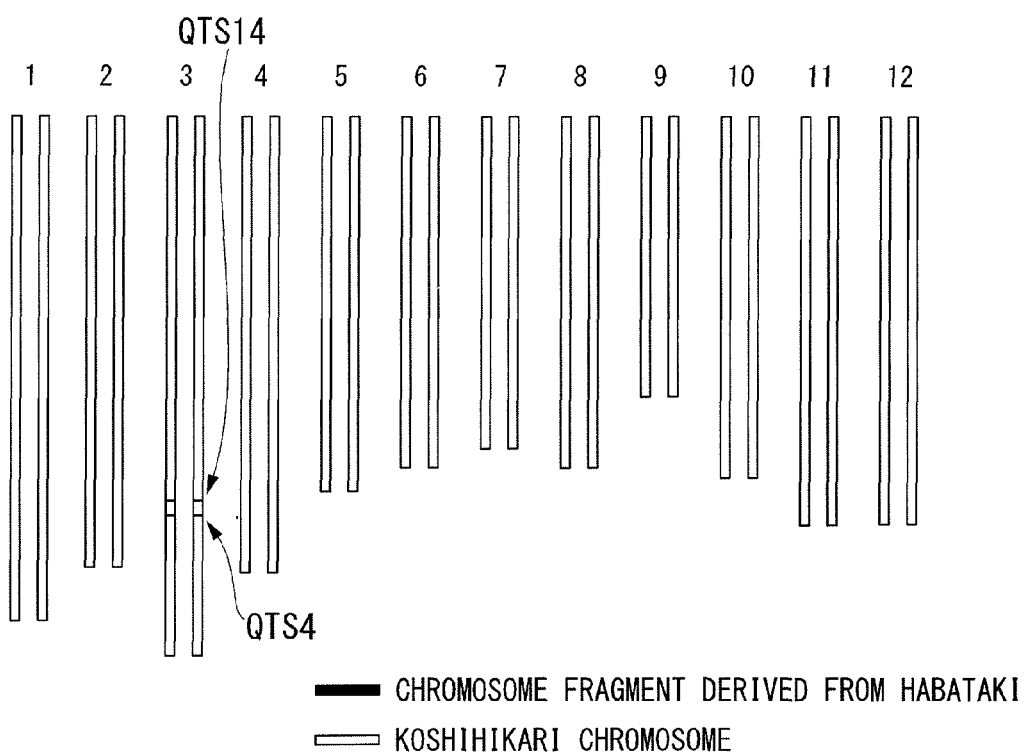
FIG. 6 is a drawing schematically representing the genome of Koshihikari kazusa no. 5.

The selected cultivated individuals were then allowed to self-propagate (self-crossbreed) followed by further harvesting the progeny individuals in the form of seeds. The harvested seeds were further cultivated, and after growing to a degree that allowed them to be relocated to a field, DNA was recovered from the leaves of each cultivated individual, and a single cultivated individual was selected in which DNA marker M1-Ac and DNA marker M5-Tg were homo chromosome regions for the Koshihikari-derived allele, and DNA marker M2-Ct, DNA marker M3 (DNA marker M3-Ag) and DNA marker M4-At were homo chromosome regions for the Habataki-derived allele. This selected cultivated individual was a new cultivar in which the (QTS4+QTS14) region had been replaced with a Habataki-derived chromosome fragment, and the inventor of the present invention named this new cultivar "Koshihikari kazusa no. 5". FIG. 6 is a drawing schematically representing the genome of Koshihikari kazusa no. 5.

Moreover, when the heading time of Koshihikari kazusa no. 5 was measured in a field located in Chiba prefecture (seeding date: May 6, 2010, relocation date: Jun. 1, 2010), in contrast to the heading time of Koshihikari being August 5 to August 8, that of Koshihikari kazusa no. 5 was July 27 to July 30. FIG. 7 shows the measured results for the heading time of Koshihikari kazusa no. 5 along with the results for Koshihikari, the QTS4 homotype and the QTS14 homotype. Although Koshihikari kazusa no. 5 clearly matured somewhat earlier than the original Koshihikari cultivar, it is also clear from FIG. 7 that the heading time thereof was later than that of the QTS14 homotype.

A comparative study was conducted between the traits of Koshihikari kazusa no. 5 and Koshihikari (carried out in a field located in Chiba prefecture in 2009). Traits were examined in compliance with an examination of characteristics for application for cultivar registration based on Article 5, Paragraph 1 of the Seed and Seedlings Law of Japan (Law No. 83, 1998). The results of the study are shown in Tables 2 to 5. As a result, Koshihikari kazusa no. 5 matured about 5 to 6 days earlier than Koshihikari for both heading time and maturation time. In addition, although culm length, length of the major axis of the head and main stem length of Koshihikari kazusa no. 5 were slightly shorter than those of Koshihikari and the number of heads and number of grains on the main stem were also fewer, other traits were basically the same as those of Koshihikari.

TABLE 2

| | | Cultivar Characteristic Values (Comparison with Standard Cultivar) | | | | | | | | | Comments | Characteristics of Control Cultivars | |
| | | | | | | | | | | | (measured | Koshi- | Nippon- |
| Stage | Trait | 1 | 2 | 3 | 4 | 5 | 6 | 7 | 8 | 9 | values) | hikari | bare |
| 40 | Leaf: Anthocyanin coloring | None | | | | | | | | | Color | 1 | 1 | 1 |
| | Leaf: Anthocyanin color distribution | Tip only | Edges only | Punctate | Entire leaf | | | | | | | 1 | 1 | 1 |
| | Lear: Auricle anthocyanin color | None | | | | | | | | | Color | 1 | 1 | 1 |
| 60 | Flag leaf: Orientation of leaf body (initial) | Upright | | Semi-upright | | Horizontal | | Inverted | | | 3 | 3 | 3 |
| 90 | Flag leaf: Orientation of leaf body (later) | Upright | | Semi-upright | — | Horizontal | | Inverted | | | 4 | 4 | 4 |
| 55 | Heading time (50% heading) | Extremely early | — | Early | | Medium | | Late | | | 2 August 1 | 3 August 7 | 4 August 19 |

TABLE 2-continued

| | | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| Stage | Trait | 1 | 2 | 3 | 4 | 5 | 6 | 7 | 8 | 9 | | Koshi-hikari | Nippon-bare |
| 65 | Lemma: Apex anthocyanin coloring (initial) | None or extremely light | | Light | | Medium | | Strong | | Very strong | 1 | 1 | 1 |

TABLE 3

| | | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| Stage | Trait | 1 | 2 | 3 | 4 | 5 | 6 | 7 | 8 | 9 | | Koshi-hikari | Nippon-bare |
| 70 | Culm: length (excl. head, excl. floating rice) | Very short | | Short | | Medium | | Long | | Very long | 5<br>89.3 m | 6<br>92.1 cm | 4<br>74.7 cm |
| | Culm: Node anthocyanin coloring | None | | | | | | | | Color | 1 | 1 | 1 |
| 72-90 | Head: Major axis length | | | Short | | Medium | | Long | | | 3<br>12.7 cm | 4<br>14.4 cm | 4<br>14.2 cm |
| 70 | Head: Number | | | Few | — | Medium | | Many | | | 4<br>7.7 | 4<br>8.3 | 4<br>8.8 |
| 70-80 | Head: Awn distribution | Tip only | | Upper half | | Entirety | | | | | 1 | 1 | 1 |
| 60-80 | Spikelet: Amt. of lemma auricles | None or very few | | Few | | Medium | | Many | | Very many | Same as Koshihikari | | |
| 80-90 | Spikelet: Lemma tip color (apiculus color) | White | Yellow | Brown | Red | Violet | Black | | | | 1 | 1 | 1 |
| 90 | Head: Curvature of main axis | Upright | | Tilted | | Hanging | | Curve | | | 5 | 5 | 5 |
| | Head: Shape | Lancet | Fusiform | Rod | Broom | Spread | | | | | 2 | 2 | 2 |
| | Maturation time | Very early | | Early | — | Medium | | Late | | Very late | 4<br>9/11 | 5<br>9/17 | 6<br>9/29 |
| | Lemma color | Yellow-white | Gold | Brown | Reddish violet | Violet | Black | | | | 1 | 1 | 1 |
| | Lemma color: Pattern | None | Gold flutes | Brown flutes | Violet spots | Violet flutes | | | | | 1 | 1 | 1 |

TABLE 4

| | | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| Stage | Trait | 1 | 2 | 3 | 4 | 5 | 6 | 7 | 8 | 9 | | Koshi-hikari | Nippon-bare |
| 92 | Lemma: Apex anthocyanin coloring | None or very light | | Light | | Medium | | Dark | | Very dark | 1 | 1 | 1 |
| | Glume: Length | | | Short | | Medium | | Long | | | 3<br>1.93 mm | 3<br>1.92 mm | 3<br>1.92 mm |
| | Glume: Color | Yellow-white | Gold | Red | Violet | | | | | | 1 | 1 | 1 |
| | Hull: 1000 grain weight (maturity) | | | Small | | Medium | — | Large | | | 6<br>22.8 g | 6<br>23.1 g | 7<br>26.4 g |
| | Hull: Lemma phenol reaction | None | | Light | | Medium | | Dark | | Reacts | 1 | 1 | 1 |

TABLE 4-continued

| Stage | Trait | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| | | 1 | 2 | 3 | 4 | 5 | 6 | 7 | 8 | 9 | | Koshi-hikari | Nippon-bare |
| | Unmilled rice: Length | | | Short | | Medium | | Long | | | 5<br>5.2 mm | 5<br>5.2 mm | 6<br>5.4 mm |
| | Unmilled rice: Width | | | Narrow | | Medium | | Thick | | | 5<br>2.9 mm | 5<br>2.9 mm | 5<br>2.9 mm |
| | Unmilled rice: Shape (from side) | Round | Semi-round | Semi-fusi-form | Fusi-form | Long fusi-form | | | | | 2<br>1.8 mm | 2<br>1.8 mm | 2<br>1.9 mm |
| | Unmilled rice: Color | White | Light brown | Brown spots | Dark brown | Light red | Red | Violet spots | Vio-let | Dark violet/black | 2 | 2 | 2 |
| | Unmilled rice: Aroma | None or very weak | Weak | Strong | | | | | | | 1 | 1 | 1 |

TABLE 5

| Stage | Trait | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| | | 1 | 2 | 3 | 4 | 5 | 6 | 7 | 8 | 9 | | Koshi-hikari | Nippon-bare |
| GIII | Main stem no of grains | Very few | | Few | — | Medium | | Many | | Very many | 4<br>135 | 5<br>151 | 4<br>123 |
| | Main stem 1st internode length | Very short | | Short | | Medium | | Long | | Very long | 7<br>34.0 cm | 8<br>36.6 cm | 8<br>36.1 cm |
| | Main stem 2nd internode length | Very short | | Short | | Medium | | Long | | Very long | 5<br>21.9 cm | 6<br>22.5 cm | 5<br>17.9 cm |
| | Main stem 3rd internode length | Very short | | Short | | Medium | | Long | | Very long | 5<br>16.9 cm | 6<br>18.0 cm | 4<br>11.1 cm |
| | Main stem 4th internode length | Very short | | Short | | Medium | — | Long | | Very long | 6<br>10.2 cm | 7<br>10.5 cm | 5<br>7.5 cm |
| | Main stem 5th internode length | Very short | | Short | — | Medium | | Long | | Very long | 4<br>5.4 cm | 4<br>3.9 cm | 3<br>2.0 cm |
| | Main stem 6th internode length | Very short | | Short | | Medium | | Long | | Very long | — | — | — |
| | Main stem hull thickness | Very thin | | Thin | | Medium | | Thick | | Very thick | 5<br>2.24 mm | 5<br>2.24 mm | 5<br>2.24 mm |
| | Main stem hull length | Very short | | Short | | Medium | | Long | | Very long | 3<br>7.37 mm | 3<br>7.39 mm | 3<br>7.69 mm |
| | Main stem hull width | Very narrow | | Narrow | | Medium | | Wide | | Very wide | 5<br>3.39 mm | 5<br>3.29 mm | 5<br>3.43 mm |

INDUSTRIAL APPLICABILITY

Since the new cultivar of the present invention in the form of Koshihikari kazusa no. 5 is provided with quality and yield similar to those of Koshihikari with the exception of maturing earlier than Koshihikari, it can be used in the field of agriculture in particular. In addition, according to the method of the present invention for causing rice individuals to mature earlier, since rice individuals can be made to mature earlier than the original cultivar, this method can be used in the field of plant breeding in particular.

The invention claimed is:

1. A rice cultivar, wherein in a chromosome of rice cultivar Koshihikari, a region corresponding to a region containing base number 31,689,690 to base number 32,363,157 in a third chromosome of rice cultivar Nipponbare is homo-replaced with a chromosome fragment composed of a corresponding region of rice cultivar Habataki in a third chromosome of a rice individual, and an upstream end of the chromosome fragment is present in a region corresponding to a region containing base number 31,521,443 to base number 31,689,690 of the third chromosome of rice cultivar Nipponbare and a downstream end of the chromosome fragment is present in a region corresponding to a region containing base number 32,363,157 to base number 32,384,798 of the third chromosome of rice cultivar Nipponbare; wherein the rice cultivar is Koshihikari Kazusa no. 5, a sample of seed of said cultivar is deposited under accession number 22174.

2. A method for differentiating rice cultivars: comprising, determining whether or not a certain rice cultivar is a specific cultivar, wherein
a single nucleotide polymorphism (SNP) corresponding to the $31,521,442^{nd}$ SNP in the third chromosome of rice cultivar Nipponbare, A in rice cultivar Koshihikari and C in rice cultivar Habataki, is designated as DNA marker M1,
an SNP corresponding to the $31,689,690^{th}$ SNP of the third chromosome of rice cultivar Nipponbare, C in rice cultivar Koshihikari and T in rice cultivar Habataki, is designated as DNA marker M2,
an SNP corresponding to the $32,208,924^{th}$ SNP of the third chromosome of rice cultivar Nipponbare, A in rice cultivar Koshihikari and G in rice cultivar Habataki, is designated as DNA marker M3,
an SNP corresponding to the $32,363,157^{th}$ SNP of the third chromosome of rice cultivar Nipponbare, A in rice cultivar Koshihikari and T in the cultivar Habataki, is designated as DNA marker M4,
an SNP corresponding to the $32,384,799^{th}$ SNP of the third chromosome of rice cultivar Nipponbare, T in rice cultivar Koshihikari and G in rice cultivar Habataki, is designated as DNA marker M5, and
the DNA markers M1 to M5 are typed by genome analysis of the rice individual, and
in the case the resulting typing result is such that the DNA marker M1 is adenine (A), the DNA marker M2 is thymine (T), the DNA marker M3 is guanine (G), the DNA marker M4 is T and the DNA marker M5 is T; the rice individual is identified as rice cultivar Koshihikari kazusa no. 5, a sample of seed of said cultivar is deposited under accession number 22174.

3. A method for causing a rice individual to mature earlier than the original cultivar, comprising: homo-replacing a region corresponding to a region containing base number 31,720,064 to base number 31,724,043 of the third chromosome of rice cultivar Nipponbare with a chromosome fragment composed of the corresponding region of the rice cultivar Koshihikari Kazusa no. 5, a sample of seed of said cultivar is deposited under accession number 22174, or rice cultivar Habataki in the third chromosome of the rice individual.

4. A method for causing a rice individual to mature earlier than the original cultivar, comprising: homo-replacing a region corresponding to a region containing base number 31,720,064 to base number 32,314,677 of the third chromosome of rice cultivar Nipponbare with a chromosome fragment composed of the corresponding region of the rice cultivar Koshihikari Kazusa no. 5, a sample of seed of said cultivar is deposited under accession number 22174, or rice cultivar Habataki in the third chromosome of the rice individual.

5. The method for causing a rice individual to mature earlier than the original cultivar according to claim 4, wherein the chromosome fragment is replaced so that the upstream end of the chromosome fragment is present in a region corresponding to a region containing base number 31,689,691 to base number 31,720,064 of the third chromosome of rice cultivar Nipponbare and the downstream end of the chromosome fragment is present in a region corresponding to a region containing base number 32,314,677 to base number 32,363,156 of the third chromosome of rice cultivar Nipponbare.

6. A method for causing a rice individual to mature earlier than the original cultivar, comprising: homo-replacing a region corresponding to a region containing base number 31,689,690 to base number 32,363,157 of the third chromosome of rice cultivar Nipponbare with a chromosome fragment composed of the corresponding region of the rice cultivar Koshihikari Kazusa no. 5, a sample of seed of said cultivar is deposited under accession number 22174, or rice cultivar Habataki in the third chromosome of the rice individual.

7. The method for causing a rice individual to mature earlier than the original cultivar according to claim 6, wherein the chromosome fragment is replaced so that the upstream end of the chromosome fragment is present in a region corresponding to a region containing base number 31,521,443 to base number 3,689,690 of the third chromosome of rice cultivar Nipponbare, and the downstream end of the chromosome fragment is present in a region corresponding to a region containing base number 32,363,157 to base number 32,384,798 of the third chromosome of rice cultivar Nipponbare.

8. A method for causing a rice individual to mature later than the original cultivar, comprising: homo-replacing a region corresponding to a region containing base number 32,309,502 to base number 32,314,677 of the third chromosome of rice cultivar Nipponbare with a chromosome fragment composed of the corresponding region of the rice cultivar Koshihikari Kazusa no. 5, a sample of seed of said cultivar is deposited under accession number 22174, or rice cultivar Habataki in the third chromosome of the rice individual.

* * * * *

```
                        SEQUENCE LISTING

<160> NUMBER OF SEQ ID NOS: 15

<210> SEQ ID NO 1
<211> LENGTH: 20
<212> TYPE: DNA
<213> ORGANISM: Oryza sativa
<220> FEATURE:
<223> OTHER INFORMATION: DNA marker: Upper Primer of M1-Ac

<400> SEQUENCE: 1
cattcagttc tctcaactgc                                              20
```

<210> SEQ ID NO 2
<211> LENGTH: 22
<212> TYPE: DNA
<213> ORGANISM: Oryza sativa
<220> FEATURE:
<223> OTHER INFORMATION: DNA marker: Lower Primer of M1-Ac

<400> SEQUENCE: 2
gagattttcg aaggttcttc gc                                        22

<210> SEQ ID NO 3
<211> LENGTH: 19
<212> TYPE: DNA
<213> ORGANISM: Oryza sativa
<220> FEATURE:
<223> OTHER INFORMATION: DNA marker: SNP Primer of M1-Ac

<400> SEQUENCE: 3
ttcctaaccc agctgtgat                                            19

<210> SEQ ID NO 4
<211> LENGTH: 20
<212> TYPE: DNA
<213> ORGANISM: Oryza sativa
<220> FEATURE:
<223> OTHER INFORMATION: DNA marker: Upper Primer of M2-Ct

<400> SEQUENCE: 4
aaaacagcca cacctgatcg                                           20

<210> SEQ ID NO 5
<211> LENGTH: 20
<212> TYPE: DNA
<213> ORGANISM: Oryza sativa
<220> FEATURE:
<223> OTHER INFORMATION: DNA marker: Lower Primer of M2-Ct

<400> SEQUENCE: 5
aacatcctct gcttcctcag                                           20

<210> SEQ ID NO 6
<211> LENGTH: 20
<212> TYPE: DNA
<213> ORGANISM: Oryza sativa
<220> FEATURE:
<223> OTHER INFORMATION: DNA marker: SNP Primer of M2-Ct

<400> SEQUENCE: 6
tatcgctagc ctccatttct                                           20

<210> SEQ ID NO 7
<211> LENGTH: 21
<212> TYPE: DNA
<213> ORGANISM: Oryza sativa
<220> FEATURE:
<223> OTHER INFORMATION: DNA marker: Upper Primer of M3-Ag

<400> SEQUENCE: 7
gaatggaatg agccatactc c                                         21

<210> SEQ ID NO 8
<211> LENGTH: 20
<212> TYPE: DNA
<213> ORGANISM: Oryza sativa
<220> FEATURE:
<223> OTHER INFORMATION: DNA marker: Lower Primer of M3-Ag

```
<400> SEQUENCE: 8
ctgcatctac acgctatacc                                              20

<210> SEQ ID NO 9
<211> LENGTH: 25
<212> TYPE: DNA
<213> ORGANISM: Oryza sativa
<220> FEATURE:
<223> OTHER INFORMATION: DNA marker: SNP Primer of M3-Ag

<400> SEQUENCE: 9
gtgatggaaa agttggaagt ttgaa                                        25

<210> SEQ ID NO 10
<211> LENGTH: 21
<212> TYPE: DNA
<213> ORGANISM: Oryza sativa
<220> FEATURE:
<223> OTHER INFORMATION: DNA marker: Upper Primer of M4-At

<400> SEQUENCE: 10
acgtggggta cagcactttg a                                            21

<210> SEQ ID NO 11
<211> LENGTH: 20
<212> TYPE: DNA
<213> ORGANISM: Oryza sativa
<220> FEATURE:
<223> OTHER INFORMATION: DNA marker: Lower Primer of M4-At

<400> SEQUENCE: 11
gtcaggaaag ttggaagagg                                              20

<210> SEQ ID NO 12
<211> LENGTH: 24
<212> TYPE: DNA
<213> ORGANISM: Oryza sativa
<220> FEATURE:
<223> OTHER INFORMATION: DNA marker: SNP Primer of M4-At

<400> SEQUENCE: 12
gatctctgac aatatcaaga agct                                         24

<210> SEQ ID NO 13
<211> LENGTH: 20
<212> TYPE: DNA
<213> ORGANISM: Oryza sativa
<220> FEATURE:
<223> OTHER INFORMATION: DNA marker: Upper Primer of M5-Tg

<400> SEQUENCE: 13
tctgagtatc tgactccacg                                              20

<210> SEQ ID NO 14
<211> LENGTH: 22
<212> TYPE: DNA
<213> ORGANISM: Oryza sativa
<220> FEATURE:
<223> OTHER INFORMATION: DNA marker: Lower Primer of M5-Tg

<400> SEQUENCE: 14
ctctcctgtc ttagaagaag ac                                           22

<210> SEQ ID NO 15
```

```
<211> LENGTH: 21
<212> TYPE: DNA
<213> ORGANISM: Oryza sativa
<220> FEATURE:
<223> OTHER INFORMATION: DNA marker: SNP Primer of M5-Tg

<400> SEQUENCE: 15
caaagttggc aactcggcat a                                           21
```